(12) United States Patent
Weon et al.

(10) Patent No.: US 8,316,689 B2
(45) Date of Patent: Nov. 27, 2012

(54) QUANTITATIVE EVALUATION OF SCRATCH-INDUCED DAMAGES ON POLYMERIC AND COATING MATERIALS

(75) Inventors: Jong Il Weon, Seoul (KR); Si Yong Song, Daejeon (KR); Jong Bae Lee, Daejeon (KR); Kil Yeong Choi, Daejeon (KR); Sung Goo Lee, Daejeon (KR); Jae Heung Lee, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 240 days.

(21) Appl. No.: 12/845,388

(22) Filed: Jul. 28, 2010

(65) Prior Publication Data

US 2011/0239748 A1   Oct. 6, 2011

(30) Foreign Application Priority Data

Apr. 5, 2010 (KR) .................. 10-2010-0030986
Apr. 5, 2010 (KR) .................. 10-2010-0030993

(51) Int. Cl.
*G01N 3/56* (2006.01)
(52) U.S. Cl. ............................................................ 73/7
(58) Field of Classification Search ............... 73/7, 104, 73/865.8, 865.9
See application file for complete search history.

(56) References Cited

U.S. PATENT DOCUMENTS

| | | |
|---|---|---|
| 7,384,806 B2 | 6/2008 | Worster et al. |
| 2009/0293585 A1* | 12/2009 | Kwon et al. ................... 73/7 |

OTHER PUBLICATIONS

Wong et al., Study of surface damage of polypropylene under progressive loading, 2004, Journal of Materials Science 39, 3293-3308.*
Rangarajan et al., Scratch visibility of polymers measured using optical imaging, Mar. 2003, Polymer Engineering and Science, vol. 43, Issue 3, p. 749.*
Lin et al., Quantitative characterization of scratch and mar behavior of polymer coatings, 2001, Materials Science and Engineering, A317, 163-170.*
J.-I. Weon et al., Quantitative Evaluation of Scratch-Induced Damages on Polymeric and Coating Materials, J Mater Sci, Feb. 3, 2010, Springer Science+Business Media.
Ki-Wan Baek et al.; "Quantitative Evaluation of Scratch Behavior for Polymeric Materials"; Polymer(Korea); vol. 33; No. 4; pp. 273-283; 2009.

* cited by examiner

*Primary Examiner* — Hezron E Williams
*Assistant Examiner* — David Z Huang
(74) *Attorney, Agent, or Firm* — Lowe Hauptman Ham & Berner, LLP

(57) ABSTRACT

Provided is a method for quantitative evaluation of mar- and scratch-induced surface damage on polymeric and coating materials. The method for quantitative evaluation of scratch-induced damage on polymeric and coating materials includes: preparing a test specimen of polymeric and coating materials; inducing a scratch damage on the surface of the test specimen; representing the scratch damage formed on the test specimen as corresponding color coordinates; and calculating a quantitated scratch damage index from a combination of a load applied to the surface of the test specimen and the color coordinates corresponding to the scratch damage.

20 Claims, 11 Drawing Sheets

(A) Simple damage        (B) Complex damage (a)   (b)   (c)

(A)             (B)

(A) Area-contact ; (a) 10N, (b) 20N, (c) 30N (B) Line-contact ; (a) 10N, (b) 20N, (c) 30N (A) RGB model
(B) HSI model

Area-contact (RGB model)

Area-contact (HIS model)

Line-contact (RGB model)

Line-contact (HIS model)

(a) control  (b) 10 N  (c) 20 N

Scratch direction (a)          (b)          (c)

QUANTITATIVE EVALUATION OF SCRATCH-INDUCED DAMAGES ON POLYMERIC AND COATING MATERIALS

CROSS-REFERENCE TO RELATED APPLICATIONS

This application claims priorities under 35 U.S.C. §119 to Korean Patent Application No. 10-2010-0030986, filed on Apr. 5, 2010, and Korean Patent Application No. 10-2010-0030993, filed on Apr. 5, 2010, in the Korean Intellectual Property Office, the disclosure of which is incorporated herein by reference in its entirety.

TECHNICAL FIELD

The present invention is related to a method for quantitative evaluation of scratch-induced damage on polymeric and coating materials, and in particular, to a method allowing quantitative evaluation of damage caused by mar and scratch on the surface of polymeric and coating materials.

BACKGROUND

Recently, there are significant interests in improving scratch damages of polymeric and coating materials because they are more susceptible to scratch damages on the surface than metals. In general, scratches are regarded as visible surface damages and grooves that the human eyes can perceive. It is well known that a number of factors such as scratch mode, scratch velocity, surface hardness, surface roughness, temperature, scratch tip geometry, fillers and additives have effects on the scratch behaviors. Especially, although mar and scratch-induced damages on the material surface are visually perceivable, it is rather troublesome to accurately and quantitatively evaluate the surface damage. Accordingly, there has been a growing concern on methods enabling precise and quantitative evaluation of scratch property of polymeric and coating materials.

The current evaluation standards including ASTM (D7027-05) and ISO (19252:2008) introduce quantitative evaluation of scratch-induced surface damage of materials. But, these standard methods emphasize only the methodological aspects of scratch formation based on experiments and focused on observation of the shape of the surface damage.

For example, ISO 19252 evaluates scratch-induced surface damage, based on the apparent shape of the trace of a scratch tip, such as ploughing, wedge formation, and cutting.

However, since such a surface damage evaluation method is subjective and dependent on the competency of the observer, the obtained results may be not reproducible, meaningful while not ensuring objectivity.

Mars occur when a relatively low load is applied to a material surface. If the load is increased beyond a certain limit, whitening phenomenon occurs. According to ASTM D7027-05, the normal load at this time point, referred to as a critical normal load, is measured to quantitatively evaluate the surface damage.

However, since the critical normal load is not a normalized value. They are scratch tip geometry dependent. In other words, a new value (i.e., material property) that normalized by the corresponding contact area, similar to the definition of yield stress ($N/m^2$) and impact resistance ($J/m$), needs to be expressed to quantify the whitening point and the initiation of cutting. Therefore, there are some problems on the reproducibility, objectivity, reliability and discrimination of results. In this context, the critical normal load is not appropriate as a factor of the quantification.

Accordingly, a more effective and quantitative evaluation method for evaluating scratch-induced surface damage of a material or its visibility is required.

SUMMARY

The present invention was made to solve the foregoing problems of the existing evaluation method of scratch-induced surface damage formed on the surface of polymeric and coating materials. The present invention is provided with a method for quantitative evaluation of scratch-induced damage on polymeric and coating materials having superiority in objectivity, reliability, reproducibility, or the like, in which a scratch is made using a scratch tip capable of area-contact or line-contact with a material surface in order to measure or analyze the degree of surface damage caused by the scratch through a scratch test under a constant load condition, and the degree of surface damage is represented by corresponding color coordinates or color difference to give a quantitated result.

The present invention is also provided with a method for quantitative evaluation of visibility of mar- and scratch-induced surface damage on polymeric and coating materials under a linearly increasing load condition, which is superior in reliability, reproducibility, or the like, in which a scratch is made using a scratch tip capable of line-contact with a material surface, and the visibility of the surface damage is quantitated with 3-dimensional (3D) color coordinates of a color model to give a quantitated scratch visibility index (SVI).

In one aspect, the present invention provides a method for quantitative evaluation of scratch-induced damage formed on the surface of polymeric and coating materials, including: preparing a test specimen of polymeric and coating materials; inducing a scratch damage on the surface of the test specimen; representing the scratch damage formed on the test specimen as corresponding color coordinates; and calculating a quantitated scratch damage index from a combination of a load applied to the surface of the test specimen and the color coordinates corresponding to the scratch damage.

Preferably, the scratch damage may be formed on the surface of the test specimen using a scratch tip capable of area-contact or line-contact.

Preferably, the scratch damage may be formed by applying a constant load to the surface of the test specimen.

Preferably, the step of representing the scratch damage as corresponding color coordinates comprises steps of: obtaining an image by scanning the scratch damage formed on the surface of the test specimen; and representing color values of the obtained image as color coordinates of a 2-dimensional (2D) or 3D color model using a color analysis software.

More preferably, the step of representing the scratch damage as corresponding color coordinates is conducted by using a color analysis profiler.

Preferably, a color analysis technique using a 2D or 3D color model may be used to analyze the scratch damage formed on the surface of the test specimen.

Preferably, the scratch damage may be in a form of simple damage, in which scratches are formed along one direction, or be in a form of complex damage, in which further scratches having another direction with the simple damage is added to the simple damaged test specimen.

Preferably, the color analysis software may be one capable of performing color analysis as a whole or as a part of the surface damage area of the test specimen.

Preferably, the color analysis software is capable of performing continuous measurement on the width and length of the whole scratch formed on the surface of the test specimen.

Preferably, when a scratch tip is in line-contact with the surface of the test specimen, the color analysis software may represent the color coordinates of each row j of the image corresponding to the scratch direction as an average value of all the color coordinate values of the row j.

In case of area-contact between the scratch tip and the surface of the test specimen, the scratch damage index is calculated on the basis of degree of scratch damage ($\Delta D$) and scratch strength ($\vec{S}_s$). In case of line-contact between the scratch tip and the surface of the test specimen, the scratch damage index is calculated on the basis of degree of scratch damage ($\Delta D$) and scratch resistance ($\vec{R}_s$).

In another aspect, the present invention provides a method for quantitative evaluation of visibility of scratch-induced damage formed on the surface of polymeric and coating materials, including: preparing a test specimen of polymeric and coating materials; inducing a scratch damage on the surface of the test specimen; scanning the scratch-induced surface damage to obtain an image; performing color analysis on the image for each pixel and profiling the change in surface damage as color coordinates using a color analysis software; and graphically representing the change in the color coordinates and a load applied to the surface of the test specimen and calculating a scratch visibility index (SVI) from a determination and a combination of the components relating only to scratch visibility.

Preferably, the scratch damage may be formed on the surface of the test specimen using a scratch tip capable of line-contact.

Preferably, the scratch damage may be formed by applying a linearly increasing load to the surface of the test specimen.

Preferably, the surface damage area of the test specimen may be analyzed using a color analysis technique using a 3-dimensional color model.

More preferably, the color analysis software may be one capable of performing color analysis as a whole or as a part of the surface damage area of the test specimen.

Preferably, the color analysis software may represent the color coordinates of each row j of the image corresponding to the scratch direction as an average value of all the color coordinate values of the row j.

More preferably, the color analysis software may be one capable of performing continuous measurement on the width and length of the whole scratch formed on the surface of the test specimen.

Preferably, the scratch visibility index may be represented as a combination [$I_c$, $S_c$, $\vec{R}_c$] of intensity ($I_c$), saturation ($S_c$) and critical scratch resistance ($\vec{R}_c$) when the onset of the surface damage of the test specimen is perceived.

More preferably, the scratch tip may be contacted with the surface of the test specimen along a horizontal direction to induce the scratch damage with a constant distance and constant speed.

The method for quantitative evaluation of scratch-induced damage on polymeric and coating materials according to the present invention allows evaluation of a degree of scratch-induced surface damage formed on the material surface as a quantitated value. By providing objectivity, it can reduce evaluation errors resulting from the operator or the evaluation environment. Accordingly, a reliable evaluation of scratch resistance is ensured.

Further, the method according to the present invention allows an objective evaluation of scratch-induced surface damage of polymeric and coating materials by representing the degree of scratch-induced damage as a quantitated scratch damage index (SDI).

In addition, by providing visibility of mar- and scratch-induced surface damage formed on polymeric and coating materials as a quantitated value, the present invention allows objective evaluation of scratch visibility. As a result, it can reduce evaluation errors resulting from the operator or the evaluation environment, and a reliable evaluation of scratch resistance is ensured.

Further, by providing the visibility of scratch-induced surface damage as a quantitated scratch visibility index (SVI), the present invention allows an objective evaluation of all scratch-induced surface damages of polymeric and coating materials.

Other features and aspects will be apparent from the following detailed description, the drawings, and the claims.

BRIEF DESCRIPTION OF THE DRAWINGS

The above and other objects, features and advantages of the present invention will become apparent from the following description of preferred embodiments given in conjunction with the accompanying drawings, in which.

DETAILED DESCRIPTION OF EMBODIMENTS

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art. The terminology used herein is for the purpose of describing particular embodiments only and is not intended to be limiting of example embodiments. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

The present invention provides a method for quantitative evaluation of mar- or scratch-induced damage formed on the surface of polymeric and coating materials, in which a scratch damage is formed under a constant load condition using a scratch tip capable of line-contact or line-contact with a material surface. The degree of the scratch damage is represented as color difference or color coordinates, and a quantitated scratch damage index (SDI) is calculated from a combination of the color difference or color coordinates and a load applied to the material surface.

As used herein, the term polymeric and coating materials refer to polymeric materials and coating materials formed on the surface of various materials. Hereinafter, the polymeric and/or coating material will be simply referred to as "material".

Figure 1:
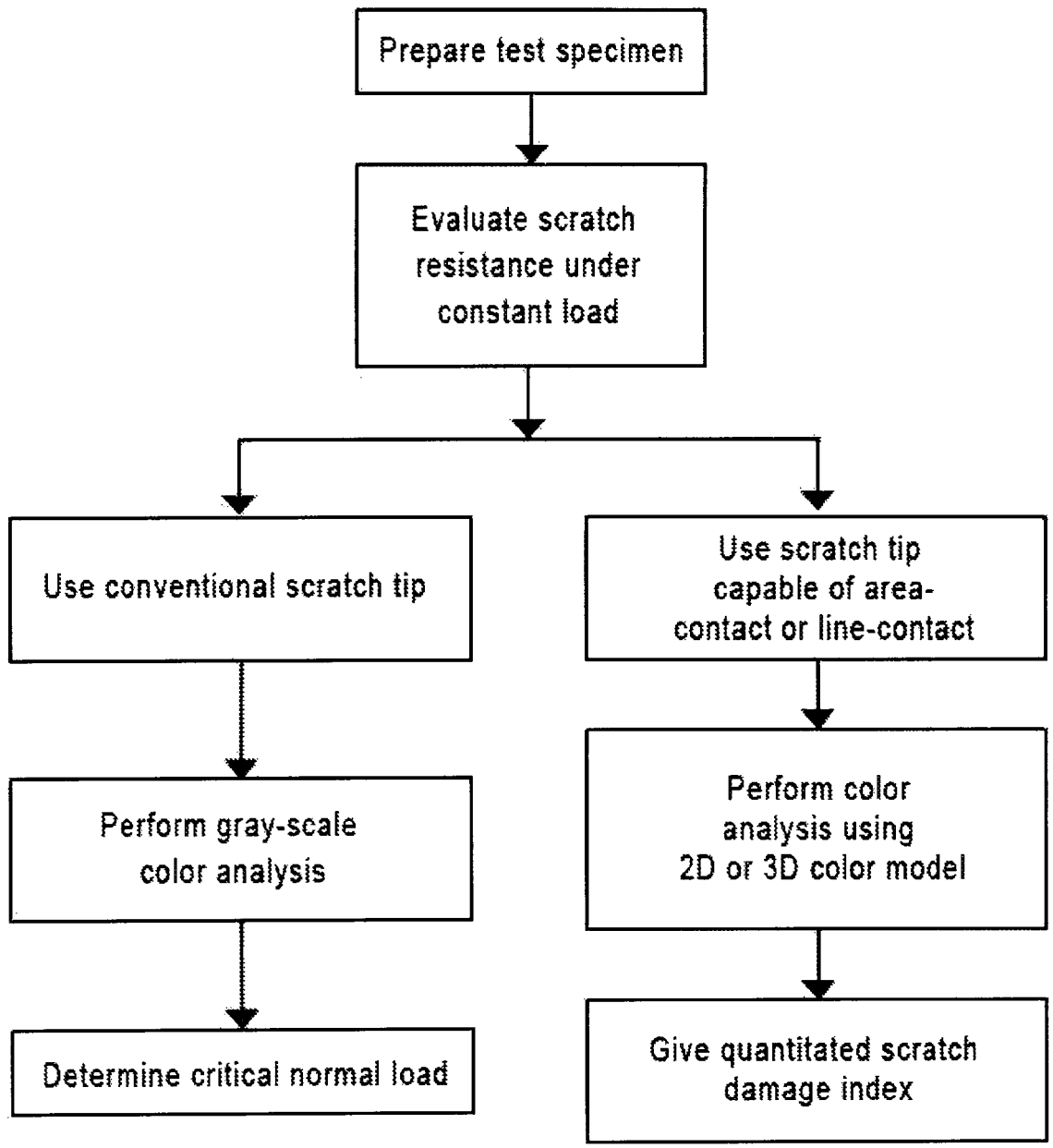
FIG. 1 is a flow diagram comparing a method for quantitative evaluation of scratch-induced damage according to an embodiment of the present invention with an existing evaluation method.

As illustrated in FIG. 1, in order to evaluate scratch resistance against a stress applied to a material surface under a constant load condition via a scratch test, a test specimen of the selected material is prepared first. Then, a scratch damage is intentionally induced on the surface of the test specimen.

A conventional scratch generator may be used to induce the scratch damage. In an embodiment of the present invention, YMT-2 (Center for Tribology, Inc.) was used as the scratch generator.

The scratch generator has a scratch tip capable of being in area-contact or line-contact with the material surface. Preferably, the scratch tip may be made of a material having hardness greater than that of the polymeric and coating materials, for example, metal, mineral or inorganic material.

In an embodiment of the present invention, the scratch tip contacts with the material surface under a constant load condition and acts to apply a stress to form a scratch.

The surface damage induced by the scratch tip may be two types. The first type is a simple damage, in which scratches or mars are formed along one direction on the material surface by the scratch tip. The other type is a complex damage, in which further scratches or mars having another direction with the simple damage is added to the simple damaged surface. The method according to the present invention evaluates both types of scratch damage.

Figure 2:
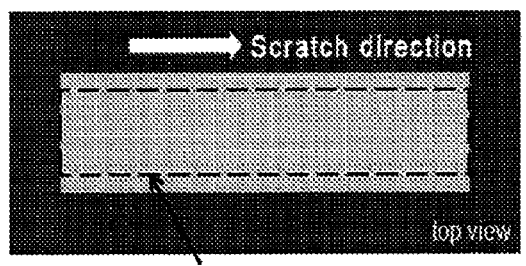
FIG. 2 shows scratches intentionally induced on a material surface under a constant load condition according to an embodiment of the present invention.
Figure 2:
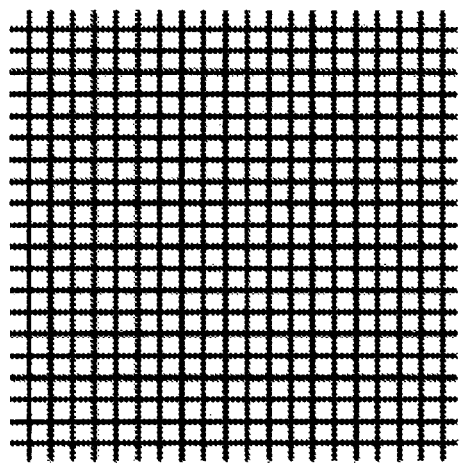

As illustrated in FIG. 2, the complex scratch damage may be formed by inducing a scratch damage along a longitudinal direction on a material surface on which a scratch damage has been already induced along a transverse direction.

Figure 3:
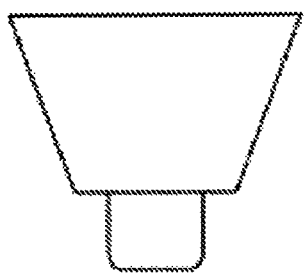
FIG. 3 shows a scratch tip used in an embodiment of the present invention.
Figure 3:
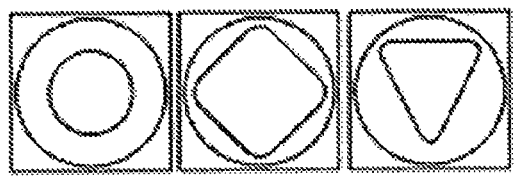
Figure 3:
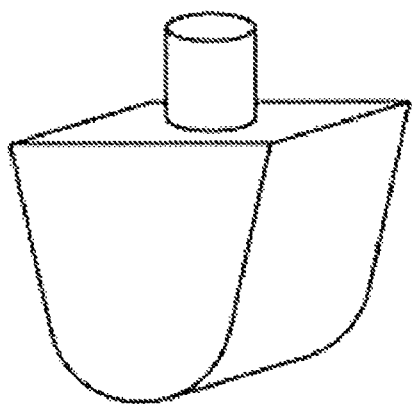

FIG. 2 schematically shows scratch damages intentionally induced on a material surface using a scratch tip according to an embodiment of the present invention;

Through area-contact or line-contact with the surface, the scratch tip is applied with a constant load on the material surface so as to induce a mar or scratch. If area-contact is desired, the contact portion of the scratch tip may have a polygonal shape, e.g. triangular or rectangular shape, or circular shape as shown in FIG. 3.

In an embodiment of the present invention, after the surface damage is induced on the surface of the test specimen, a digitized image of the surface damage area is obtained, for example, using a scanner.

Preferably, the surface damage area is scanned at a 24-bit color scale with a resolution of 600*600 dpi or better to obtain a clear and distinct image of the material surface. In an embodiment of the present invention, Perfection V700 Photo (Epson) may be used to obtain the image.

Thus obtained digital image of the surface damage area of the scratched test specimen is analyzed using a color analysis software.

The color analysis software may be a software capable of obtaining color coordinates using various 2-dimensional or 3-dimensional color models. In an embodiment of the present invention, degree of the scratch-induced damage on the material surface and scratch resistance of the material may be evaluated using the software.

In an embodiment of the present invention, the commercially available color analysis software QWin is used and the analysis result is represented as color coordinates of RGB and HSI 3-dimensional color models.

The color coordinates are composed of three components to express color for each pixel of the scanned (digitized) image. For example, in an RGB color model, the color coordinate is represented with red (R), green (G) and blue (B) values, and in an HSI color model, it is represented with hue (H), saturation (S) and intensity (I) values.

Preferably, the color analysis software is one capable of performing continuous measurement on the width and length of the whole scratch formed on the material surface as well as arbitrary selective measurement on the damage area.

Preferably, when the scratch tip is in line-contact with the surface of the test specimen, the color analysis software may represent the color coordinates of each row j of the image corresponding to the scratch direction as an average value of all the color coordinate values of the row j, for the whole or arbitrarily selected damaged area of the material surface.

More specifically, the color analysis software may classify the pixels of the image along the scratch direction for the whole or arbitrarily selected area into different rows j and represent the color coordinates of each row j of the image corresponding to the scratch direction as an average value of all the color coordinate values of the row j.

In an embodiment of the present invention, instead of scanning the damage area of the material surface, the surface damage may be directly represented as color difference or color coordinates using a color analysis profiler such as a spectrocolorimeter, a colorimeter, a color reader, or the like.

The color difference is represented as the difference in color coordinates between the area where the mar or scratch was formed and the other area.

In an embodiment of the present invention, a CM-3700d spectrocolorimeter (Konica Minolta) may be used.

Preferably, the color analysis using the spectrocolorimeter is performed under a standard condition of D65 standard illuminant, d/8 diffuse illumination and specular component excluded (SCE) mode, for objective and reasonable measurement.

Base on the color difference or color coordinates, a scratch damage index is calculated as a quantitated value of the scratch-induced surface damage.

The scratch damage index is represented by degree of scratch damage ($\Delta D$), scratch strength ($\vec{S}_s$) and scratch resistance ($\vec{R}_s$). The representation may be different depending on the kind of the scratch tip.

For example, if the scratch tip contacts the material surface with a constant area, i.e. area-contact, the scratch damage index may be represented by [$\Delta D$, $\vec{S}_s$]. And, if the scratch tip contacts linearly with the material surface, i.e. line-contact, it may be represented by [$\Delta D$, $\vec{R}_s$].

Here, the degree of scratch damage ($\Delta D$) is calculated as the Euclidean distance between the color coordinates of the scratch-induced portion x and the intact portion y to give a quantitated value of the scratch-induced surface damage. The distance between the two portions is calculated by Equation 1. The scratch strength ($\vec{S}_s$) and the scratch resistance ($\vec{R}_s$) are calculated by Equations 2 and 3.

$$\Delta D(x, y) = \|x - y\| = \sqrt{\sum_{i=1}^{n} (x_i - y_i)^2} \quad \text{Equation 1}$$

$$\vec{S}_s = \vec{F}_s / A \quad \text{Equation 2}$$

$$\vec{R}_s = \vec{F}_s / l \quad \text{Equation 3}$$

wherein A is the contact area between the scratch tip and the material surface, and l is the contact length between the scratch tip and the material surface.

The scratch force ($\vec{F}_s$) applied to the surface is defined as the summation of two orthogonal vectors, normal load ($\vec{F}_n$) and resulting tangential load ($\vec{F}_t$) as shown in Equation 4.

Here, the normal load ($\vec{F}_n$) is a load applied by the scratch tip in a direction perpendicular to the material surface, and the tangential load ($\vec{F}_t$) is a load applied by the scratch tip in a direction parallel to the material surface.

$$\vec{F}_s = \vec{F}_n + \vec{F}_t \quad \text{Equation 4}$$

Figure 4:
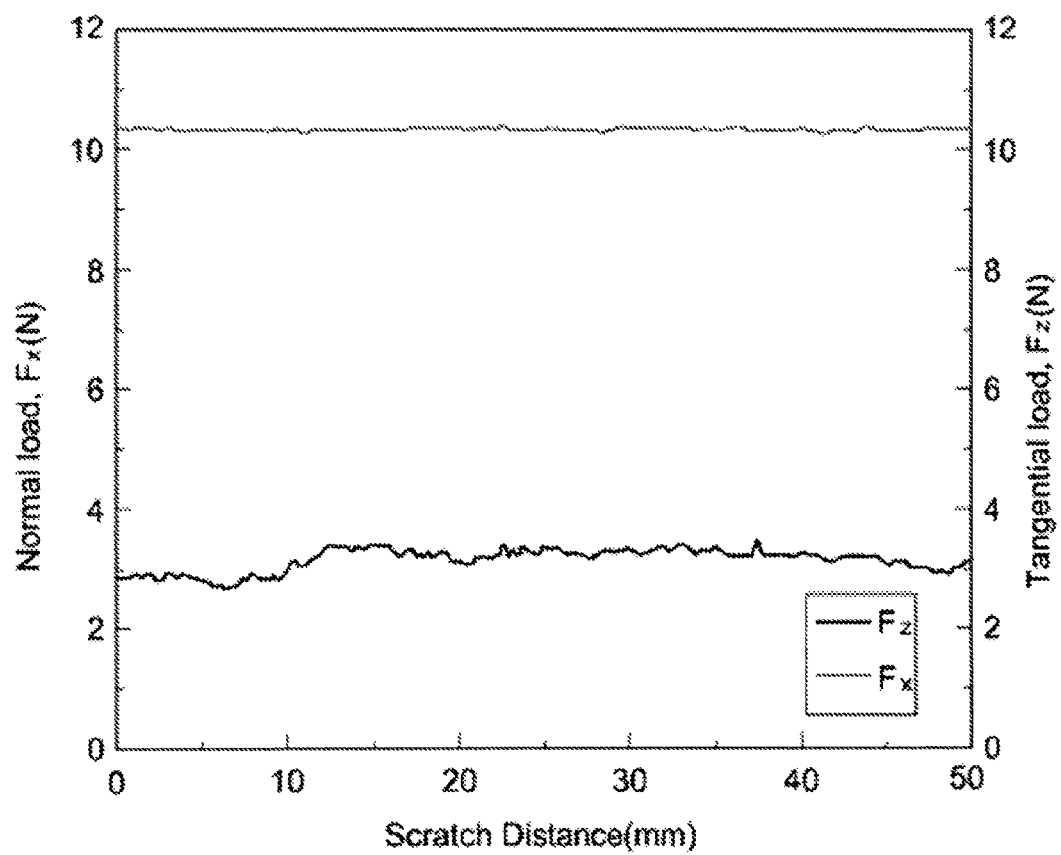
FIG. 4 graphically shows the raw data obtained from a scratch test under a constant load condition according to an embodiment of the present invention.

FIG. 4 graphically shows the raw data obtained from a scratch test under a constant load condition according to an embodiment of the present invention.

In the present invention, there is no specific limitation on the thickness of the test specimen. However, a plate-type test specimen having a thickness 10 mm or smaller and a length 70 mm or longer is preferred.

EXAMPLES

The examples and experiments will now be described. The following examples and experiments are for illustrative purposes only and not intended to limit the scope of this disclosure.

Example 1

A 3-mm thick, plate-type polypropylene composite material was used as a test specimen for evaluation of scratch damage.

Mar and Scratch of Simple Damage

A 50-mm long scratch was formed along one direction on the test specimen using a scratch generator. The scratching speed (the speed at which the scratch damage was formed) was fixed at 1 mm/s, and the load to form the scratch was varied at 10 N, 20 N and 30 N.

The scratch tip to form the scratch on the test specimen was that of FIG. 3 (A)(a) or (B). In case of area-contact, a scratch tip having the shape of FIG. 3 (A)(a) and contacting with the test specimen with a contact diameter of 1 mm and a contact area of 0.785 mm² was used. In case of line-contact, one having the shape of FIG. 3 (B) and contacting with the test specimen with a contact length of 1 mm was used.

After the surface damage was formed on the surface of the test specimen, a digital image was obtained using a flatbed scanner.

Figure 5:
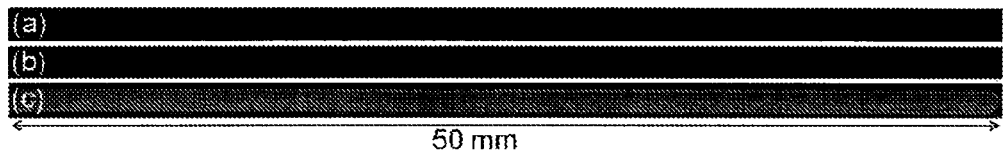
FIG. 5 shows digitized images of simple damages obtained using a flatbed scanner according to an embodiment of the present invention.
Figure 5:
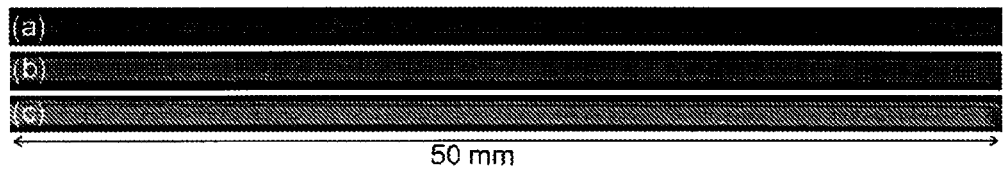

FIG. 5 shows digitized images of the mar- and scratch-induced simple damages obtained using the flatbed scanner.

In this example, about 90% of the total width of the scratch was arbitrarily selected, and color analysis was performed using two 3-dimensional color models of RGB and HSI.

Figure 6:
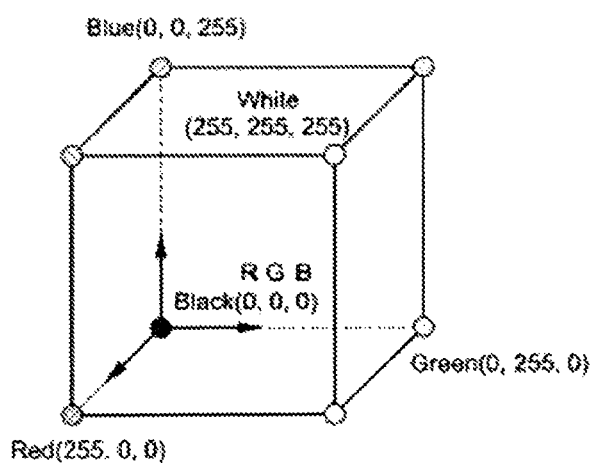
FIG. 6 shows 3-dimensional color models and the range of color coordinate values according to an embodiment of the present invention.
Figure 6:
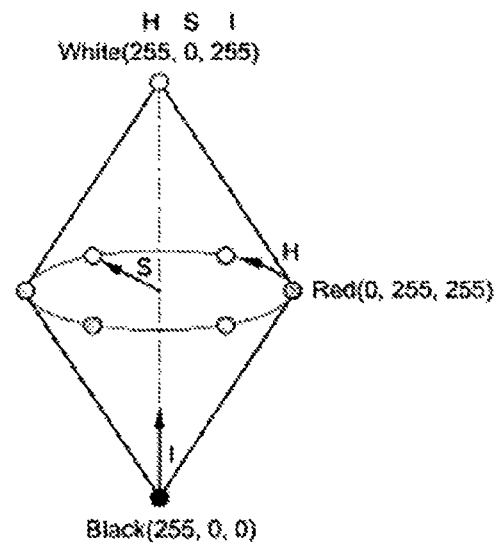
Figure 7A:
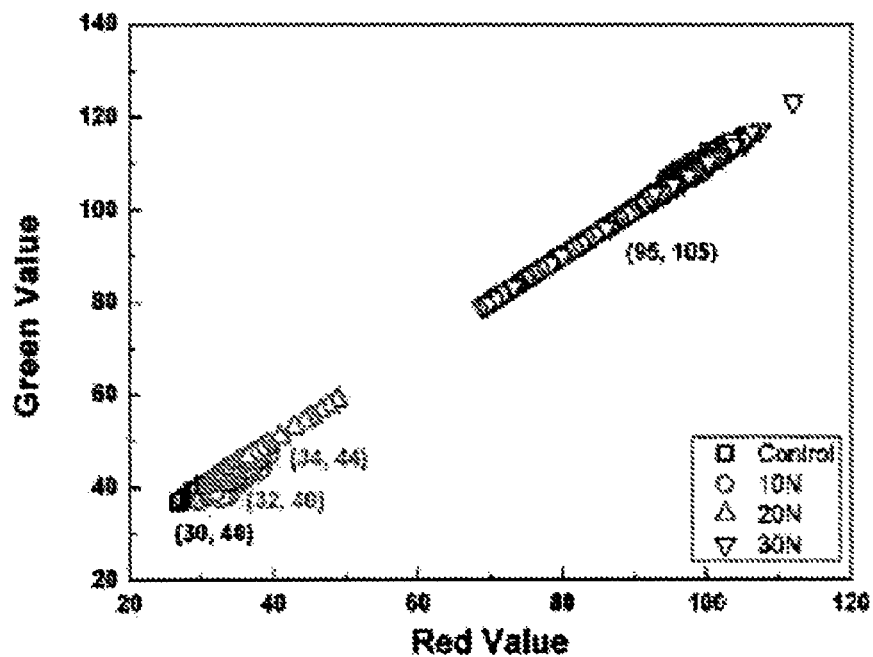
FIGS. 7A-7D graphically show color analysis result according to an embodiment of the present invention.
Figure 7B:
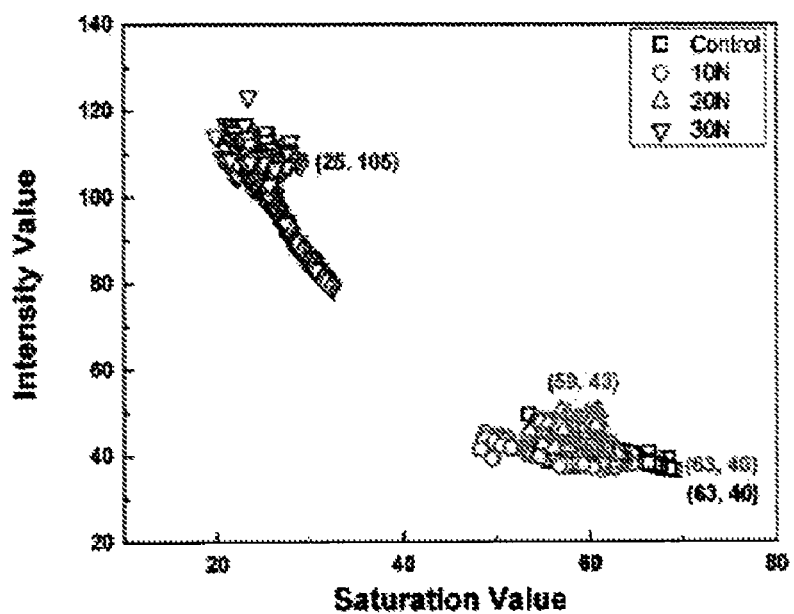
Figure 7C:
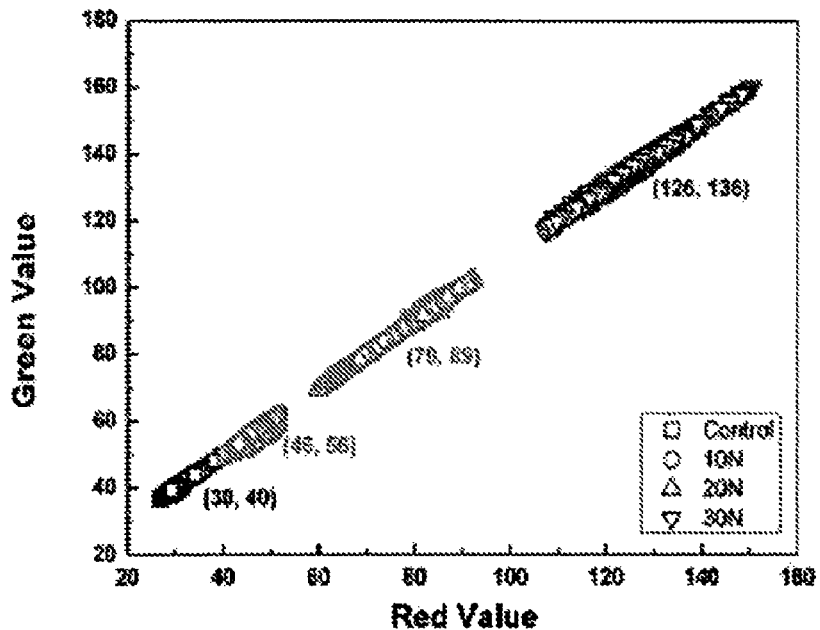
Figure 7D:
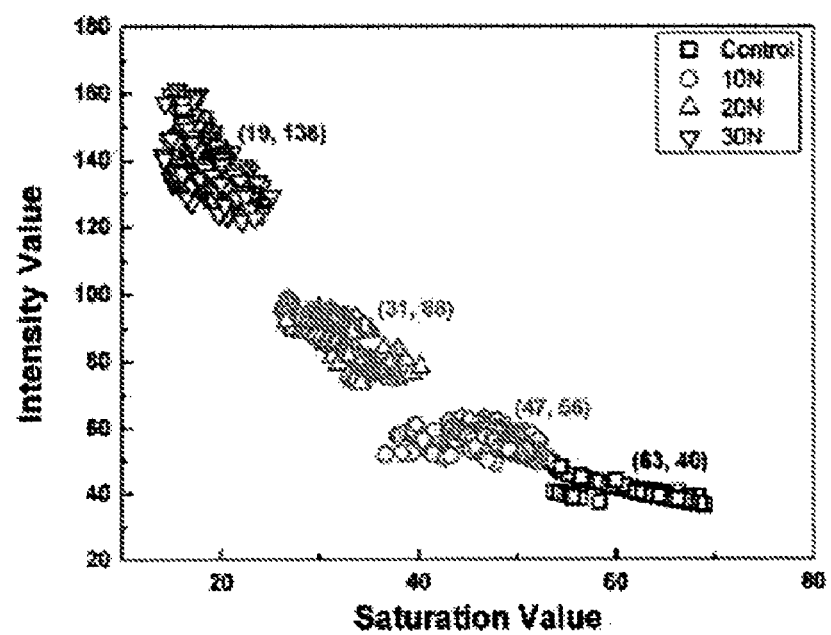

FIG. 6 schematically shows the color coordinate values of the RGB and HSI color models, and FIGS. 7A-7D graphically show the color analysis result of Example 1 using the RGB and HSI color models in 2 dimensions. The color analysis result (mean and standard deviation) of FIGS. 7A-7D is given in Table 1.

As shown in Table 1, as the constant load applied to the test specimen increased, so did the color coordinate values of the RGB color model. In contrast, in the HSI color model, the intensity ($I_m$) and the saturation ($S_m$) values showed opposite behaviors with the increase of the constant load. That is to say, as the constant load applied to the test specimen increased, the intensity ($I_m$) value increased but the saturation ($S_m$) decreased.

From a combination of the color coordinates presented in Table 1 with the applied load, the quantitated 'scratch damage index (SDI)' was calculated and given in Table 2.

As seen from Tables 1 and 2, the method for evaluation of the scratch-induced surface damage according to the present invention gives the degree of surface damage as a digitized value.

In Tables 1 and 3 that follow, "control" means a test condition with no scratch damage formed.

TABLE 1

| Test condition | Area-contact | | | | Line-contact | | | |
| --- | --- | --- | --- | --- | --- | --- | --- | --- |
| | RGB | | HSI | | RGB | | HSI | |
| | $G_m$ | $R_m$ | $I_m$ | $S_m$ | $G_m$ | $R_m$ | $I_m$ | $S_m$ |
| Control | 40 ± 1.8 | 30 ± 1.8 | 40 ± 1.8 | 63 ± 3.1 | 40 ± 1.8 | 30 ± 1.8 | 40 ± 1.8 | 63 ± 3.1 |
| 10 N | 40 ± 1.3 | 32 ± 1.4 | 40 ± 1.2 | 63 ± 2.5 | 56 ± 2.2 | 46 ± 2.2 | 56 ± 2.2 | 47 ± 2.4 |
| 20 N | 44 ± 2.3 | 34 ± 2.3 | 43 ± 1.9 | 59 ± 1.8 | 89 ± 6.3 | 79 ± 6.2 | 88 ± 4.5 | 31 ± 2.0 |
| 30 N | 105 ± 6.3 | 95 ± 6.2 | 105 ± 6.3 | 25 ± 1.8 | 136 ± 6.9 | 126 ± 7.1 | 138 ± 5.9 | 19 ± 1.8 |

TABLE 2

| Test condition | Scratch damage index (SDI) | | | |
| --- | --- | --- | --- | --- |
| | Area-contact | | Line-contact | |
| | RGB [ΔD, $\vec{S}_s$] | HSI [ΔD, $\vec{S}_s$] | RGB [ΔD, $\vec{R}_s$] | HSI [ΔD, $\vec{R}_s$] |
| 10N | [2.0, 12.8] | [0, 12.8] | [22.6, 10.3] | [22.6, 10.3] |
| 20N | [5.7, 25.3] | [5.0, 25.3] | [69.3, 21.5] | [57.7, 21.5] |
| 30N | [91.9, 40.0] | [75.3, 40.0] | [135.8, 34.1] | [107.4, 34.1] |

Mar and Scratch of Complex Damage

First, 20 simple damages were formed on the test specimen with 3 mm intervals along a transverse direction using a scratch tip capable of line-contact with the material surface. Then, 20 scratch damages were formed with 3 mm intervals in a longitudinal direction to induce complex damages.

Figure 8:
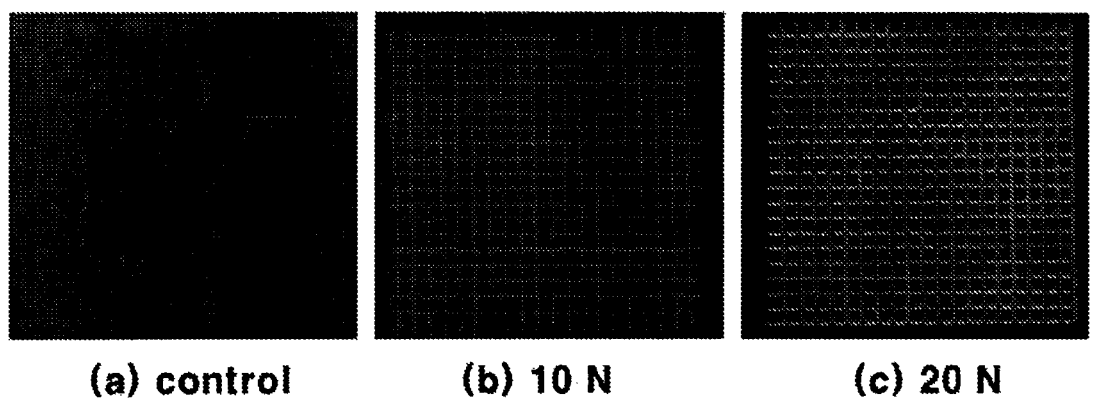
FIG. 8 shows digitized images of complex damages obtained using a flatbed scanner according to an embodiment of the present invention.

FIG. 8 shows digitized images of the complex damages obtained using a flatbed scanner. (a) is the image when no scratch damage was formed on the surface of the test specimen, (b) is the image when a scratch damage was formed by applying a load of 10 N, and (c) is the image obtained when a scratch damage was formed by applying a load of 20 N.

After the complex damages were induced on the test specimen as in FIG. 8, D65 standard illuminant, d/8 diffuse illumination, specular component excluded mode color analysis was performed using a spectrocolorimeter under a condition of D65 standard illuminant, d/8 diffuse illumination and specular component excluded (SCE) mode. A measuring mirror having a diameter of 25.4 mm was used. Then, the degree of the damage of the surface of the test specimen by the complex damage was represented as color difference (ΔL) by comparing the color coordinates of scratched portion with those of intact portion, using the L*a*b* color model.

Of course, as in the simple damage, the degree of mar and scratch by the complex damage may also be quantitated using a color analysis software after scanning the complex damage area to obtain an image.

Table 3 shows the degree of the damage of the surface of the test specimen by the complex damage as mean and standard deviation of the color difference (ΔL).

TABLE 3

| Test condition | Area-contact ΔL (change in lightness) |
| --- | --- |
| Control | — |
| 10N | 2.7 ± 0.4 |
| 20N | 4.5 ± 0.4 |

The scratch-induced surface damage analysis in Example 1 gives objective and quantitated values, with less evaluation errors resulting from the operator or the evaluation environment and high reliability and reproducibility.

As described above, the present invention provides a method for quantitative evaluation of mar- or scratch-induced damage formed on the surface of polymeric and coating materials, whereby a scratch damage is intentionally formed using a scratch tip capable of line-contact or line-contact with a material surface, the degree of the scratch damage is represented as color difference or color coordinates after obtaining a digitized image of the surface damage area by scanning and using a color analysis software or using a color analysis profiler such as a spectrocolorimeter, a colorimeter or a color reader without acquisition of the digitized image, and a quantitated scratch damage index is calculated therefrom.

By performing color analysis on the surface of polymeric and coating materials on which scratch damage is formed and providing the evaluation result as a quantitated scratch damage index, the present invention allows quantitative evaluation of the scratch-induced surface damage.

The present invention is applicable without regard to the color or surface pattern of the material surface. And, the operator may randomly select the color model for analysis of the surface damage without limitation.

The present invention also provides a method for quantitative evaluation of visibility of scratch-induced damage formed on the surface of polymeric and coating materials, comprising: preparing a test specimen of polymeric and coating materials; inducing a scratch damage on the surface of the test specimen; scanning the scratch-induced surface damage to obtain an image; performing color analysis on the image for each pixel and profiling the change in surface damage as color coordinates using a color analysis software; and graphically representing the change in the color coordinates and a load applied to the surface of the test specimen and calculating a scratch visibility index (SVI) from a determination and a combination of the components relating only to scratch visibility.

Figure 9:
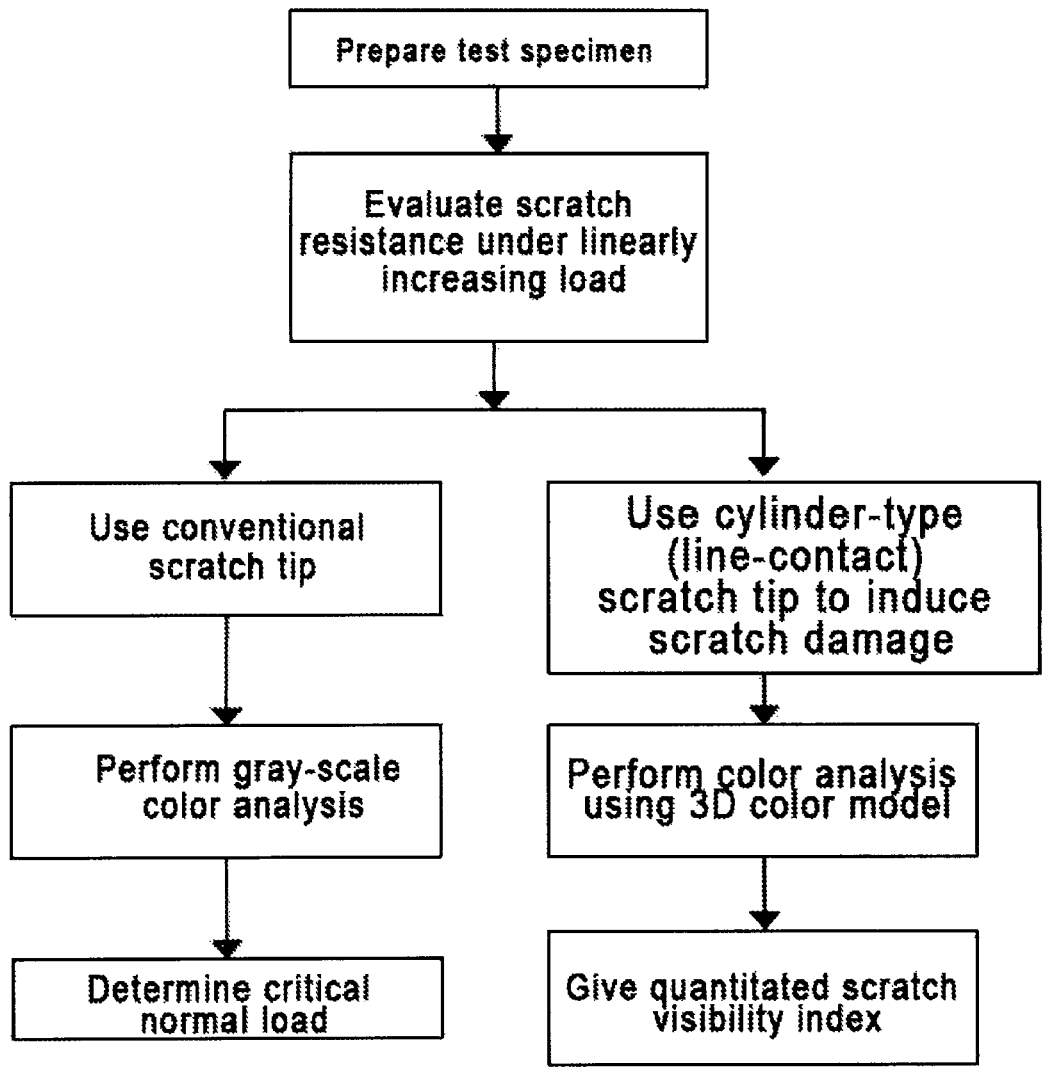
FIG. 9 is a flow diagram comparing a method for quantitative evaluation of visibility of scratch-induced damage on polymeric and coating materials according to an embodiment of the present invention with an existing evaluation method.

As illustrated in FIG. 9, in order to evaluate scratch resistance under a linearly increasing load condition via a scratch test, a test specimen of the selected material is prepared first. Then, a scratch damage is intentionally induced on the surface of the test specimen.

The scratch test is performed under a linearly increasing load condition in order to form a scratch damage on the surface of the test specimen. A commonly used scratch generator may be used to induce the scratch damage. In an embodiment of the present invention, YMT-2 (Center for Tribology, Inc.) may be used as the scratch generator.

The scratch generator, which is used to intentionally induce mar or scratch on the surface of the test specimen, has a scratch tip capable of line-contact with the material surface. Preferably, the scratch tip may be made of a material having hardness greater than that of the polymeric and coating materials, for example, metal, mineral or inorganic material.

In an embodiment of the present invention, the scratch tip the contacts with the material surface under a linearly increasing load condition and acts to apply a stress to form a scratch.

To this end, the scratch generator controls the scratch tip to apply a linearly increasing load to the surface of the test specimen.

The scratch tip is contacted with the surface of the test specimen along a horizontal direction under a linearly increasing load (e.g., 1 to 30 N) condition with a constant distance (length) or constant speed.

In other words, in order to induce the scratch damage on the surface of the test specimen, the scratch tip is contacted with the surface of the test specimen along a horizontal direction and applies a linearly increasing load with a constant distance and constant speed.

Figure 10:
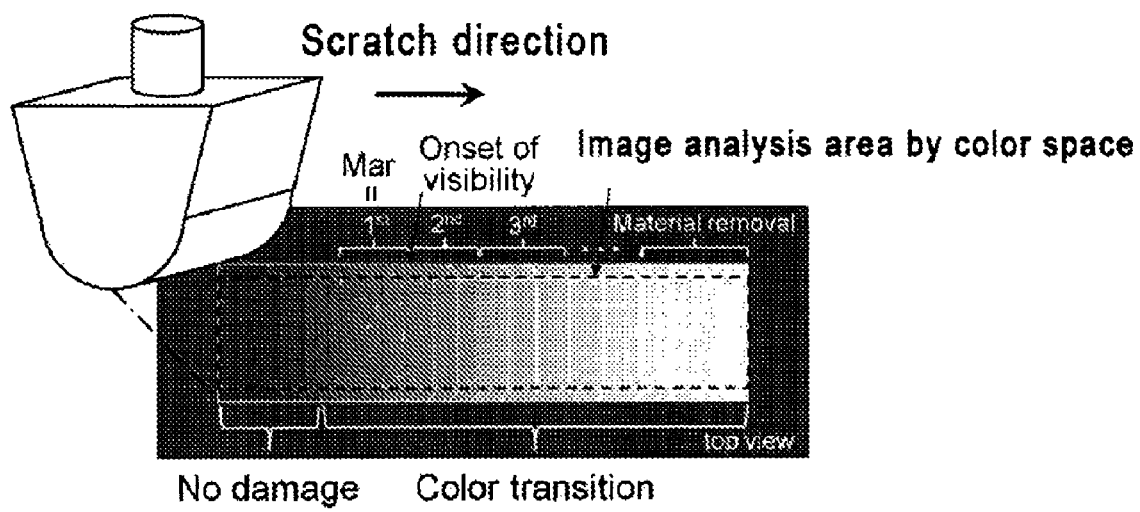
FIG. 10 schematically shows a scratch tip used in an embodiment of the present invention and a surface damage induced under a linearly increasing load condition according to an embodiment of the present invention.

FIG. 10 schematically shows a scratch tip used in an embodiment of the present invention and a surface damage induced under a linearly increasing load condition according to an embodiment of the present invention. As shown in the figure, as a linearly increasing load is applied to the surface of the test specimen along the scratch direction, first ($1^{st}$), second ($2^{nd}$) and third ($3^{rd}$) color transitions occur sequentially.

After the surface damage is induced on the surface of the test specimen, a digitized image of the surface damage area is obtained, for example, using a scanner.

Preferably, the surface damage area is scanned at a 24-bit color mode of a resolution of 1400*600 dpi or better to obtain a clear and distinct image of the material surface. In an embodiment of the present invention, Perfection V700 Photo (Epson) may be used to obtain the image.

Thus obtained digital image of the surface damage area of the scratched test specimen is analyzed using a color analysis software. As a result, the surface damage is computed as three color coordinate values of a 3D color model along the scratch path of the input image.

The color analysis software may be a software capable of representing the change of surface damage along the scratch path of the image as color coordinate values of a 3D color model. In an embodiment of the present invention, visibility of the scratch-induced damage may be evaluated using the software.

In an embodiment of the present invention, the commercially available color analysis software QWin is used and the analysis result is represented as color coordinates of RGB and HIS 3D color models.

Figure 11:
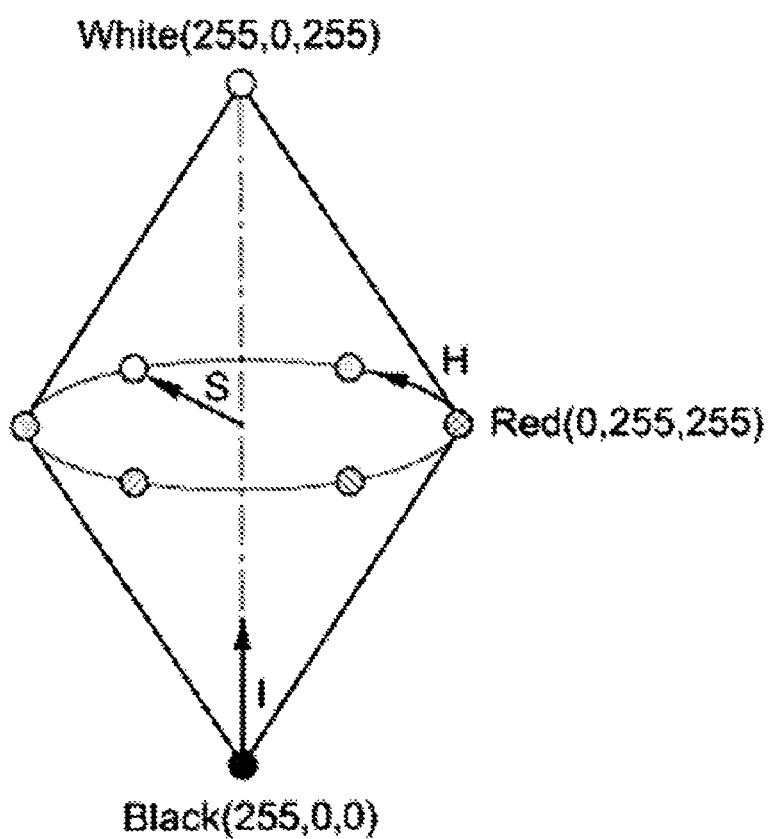
FIG. 11 schematically shows color coordinates of an HSI color model.

The color coordinates are represented by three different components each representing inherent color values for each pixel of the digitized image. For example, in an RGB color model, the color coordinates are represented as red (R), green (G) and blue (B) values, and in an HSI color model, they are represented hue (H), saturation (S) and intensity (I) values, as illustrated in FIG. 11.

Hue is the component representing the color itself, saturation is the component representing how much white color is included, and intensity is the component representing the lightness (intensity) of the color. Each component is represented by an integer value from 0 to 255. Each pixel of the scanned image may be represented by a combination of the three color components, i.e. color coordinates.

Preferably, the color analysis software is one capable of performing continuous measurement on the width and length of the whole scratch formed on the material surface as well as arbitrary selective measurement on the damage area.

Figure 12:
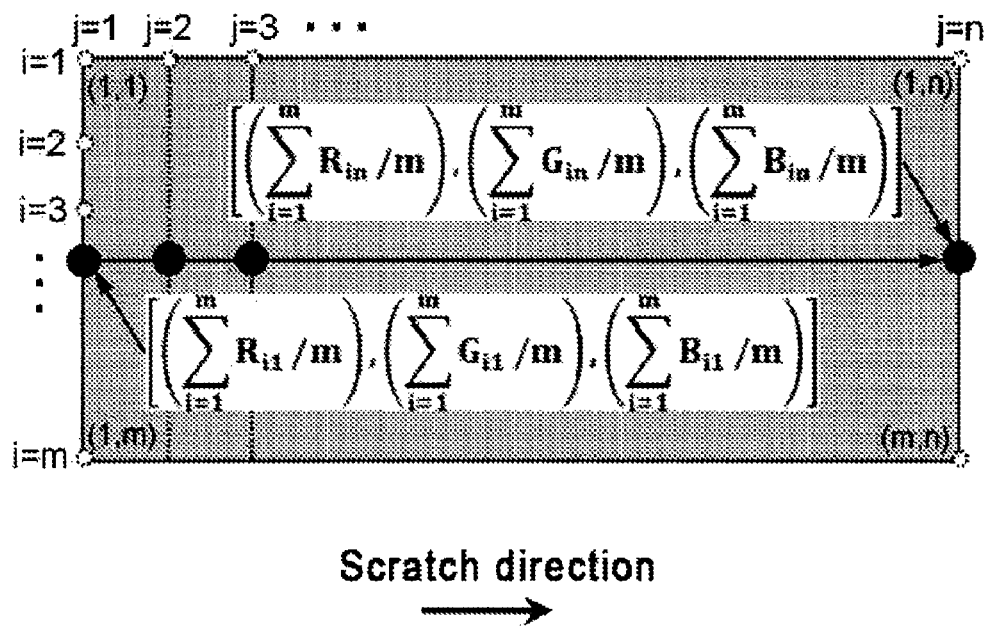
FIG. 12 schematically illustrates a method of obtaining color coordinate values representing each row of an image using a color analysis software according to an embodiment of the present invention.

Preferably, when the color analysis software performs analysis on an arbitrarily selected damaged area of the material surface, the color coordinate values of each row j of the image corresponding to the scratch direction may be represented as an average value of all the color coordinate values of the row j, as $[R_j, G_j, B_j]$, as shown in FIG. 12, which are defined as in Equation 5.

$$R_j = \sum_{i=1}^{m} R_{ij}/m \qquad \text{Equation 5}$$

$$G_j = \sum_{i=1}^{m} G_{ij}/m$$

$$B_j = \sum_{i=1}^{m} B_{ij}/m$$

FIG. 12 schematically illustrates a method of obtaining color coordinate values representing each row of an image using a color analysis software according to an embodiment of the present invention. The color analysis software may classify the pixels of the image along the scratch direction for the whole or arbitrarily selected area into different rows j and represent the color coordinates of each row j of the image corresponding to the scratch direction as an average value of all the color coordinate values of the row j.

In case of an HSI color model, the color coordinates representing each row j of the image may be defined as in Equation 6, similarly to the RGB color model.

$$H_j = \sum_{i=1}^{m} H_{ij}/m \qquad \text{Equation 6}$$

$$S_j = \sum_{i=1}^{m} S_{ij}/m$$

$$I_j = \sum_{i=1}^{m} I_{ij}/m$$

Accordingly, the color coordinates representing each row j of the surface damage image along the scratch direction may be represented as $[R_j, G_j, B_j]$ or $[H_j, S_j, I_j]$.

Based on the color analysis result, the change in the color coordinates along the scratch path and the increase in the applied load are graphically represented to calculate the quantitated scratch visibility index (SVI).

The scratch visibility index may be represented as a combination of intensity ($I_c$), saturation (Se) and critical scratch resistance (c) when the onset of the surface damage of the test specimen is perceived. In an embodiment of the present invention, the scratch visibility index is defined by Equation 7.

$$\text{SVI}=[I_c, S_c, \vec{R}_c] \qquad \text{Equation 7}$$

wherein $I_c$ and $S_c$ are respectively intensity and saturation when the onset of the surface damage of the test specimen is perceived, i.e., intensity and saturation at the onset of scratch visibility which will be described later.

The scratch resistance ($\vec{R}_s$) is calculated by Equation 8.

$$\vec{R}_s = \vec{F}_s/l \qquad \text{Equation 8}$$

wherein l is a contact length of the scratch tip with the material surface, and the critical scratch resistance ($\vec{R}_c$) is the scratch resistance ($\vec{R}_s$) when the onset of the surface damage of the test specimen is perceived.

And, the scratch force ($\vec{F}_s$) by which the scratch damage is applied to the test specimen as the scratch tip is in line-contact is a vector sum of normal ($\vec{F}_n$) and tangential load ($\vec{F}_t$) as shown in Equation 9.

Here, the normal load ($\vec{F}_n$) is a load applied by the scratch tip in a direction perpendicular to the material surface, and the tangential load ($\vec{F}_t$) is a load applied by the scratch tip in a direction parallel to the material surface.

$$\vec{F}_s = \vec{F}_n + \vec{F}_t \qquad \text{Equation 9}$$

The thickness of the test specimen used in an embodiment of the present invention for quantitative evaluation of the visibility the scratch damage is not particularly limited. A plate-type test specimen having a thickness 10 mm or smaller and a length 70 mm or longer is preferred.

Example 2

A 3-mm thick, plate-type polypropylene composite material was used as a test specimen for evaluation of scratch visibility.

A 50-mm long scratch was formed on the test specimen using a scratch generator. The scratching speed (the speed at which the scratch damage was formed) was fixed at 1 mm/s, and a load increasing from 1 to 30 N was applied.

The scratch tip to form the scratch on the test specimen was that of FIG. 10. The contact length with the surface of the test specimen was 1 mm.

After the surface damage was formed on the surface of the test specimen, a digital image was obtained using a flatbed scanner.

Figure 13:
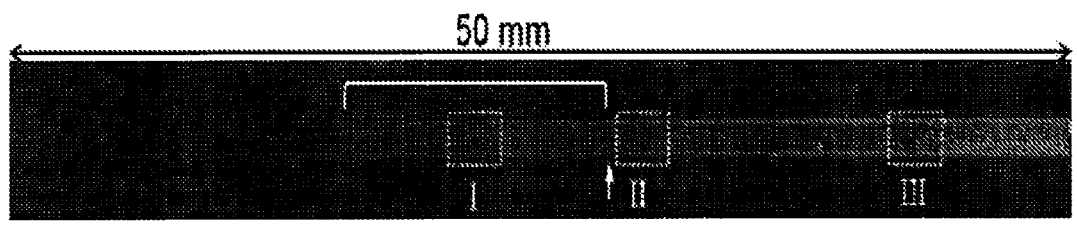
FIG. 13 shows an image of a mar- and scratch-induced surface damage obtained using a flatbed scanner according to an embodiment of the present invention.

FIG. 13 shows digitized images of the mar- and scratch-induced simple damages obtained using the flatbed scanner.

Figure 14:
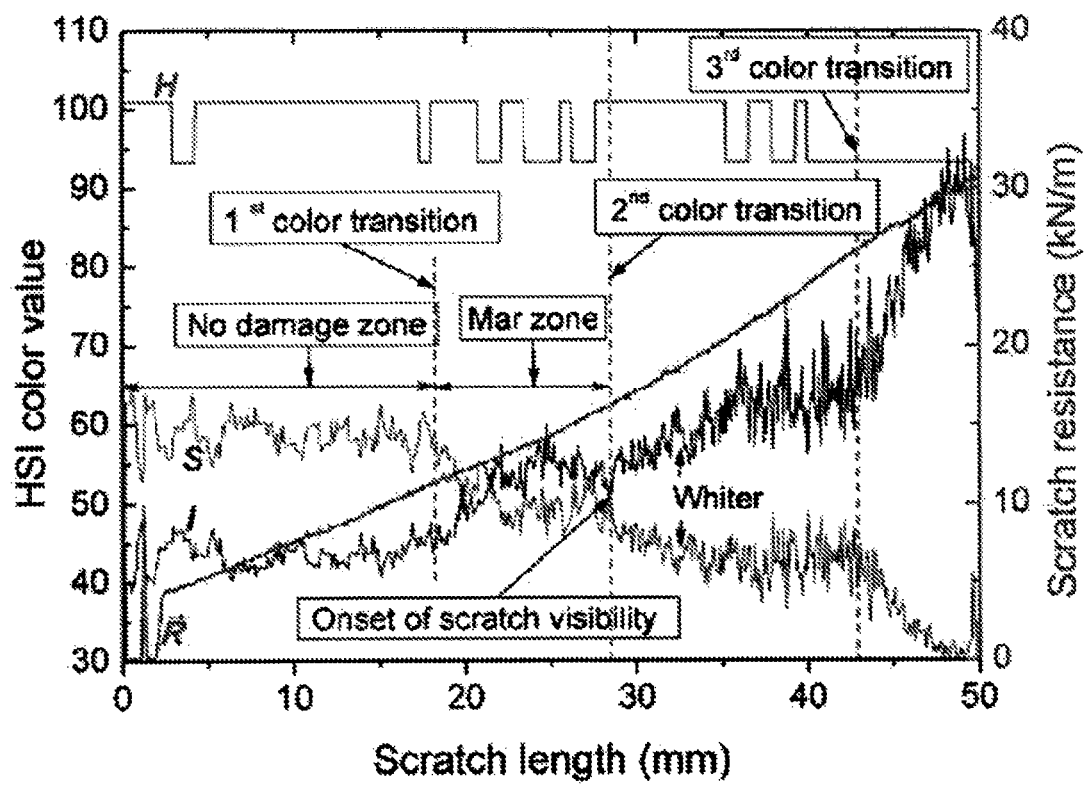
FIG. 14 graphically shows changes in color coordinates and scratch resistance as a result of a color analysis according to an embodiment of the present invention.

In this example, about 90% of the total width of the scratch was arbitrarily selected (see FIG. 10), and color analysis was performed using the HSI color model. FIG. 14 graphically shows changes in the color coordinates (H, S, I) and the scratch resistance ($\vec{R}_s$) along the scratch path.

As shown in FIG. 14, along the scratch path (i.e., as the scratch length increased), (1) the scratch resistance ($\vec{F}_s$) increased linearly, (2) the hue value (H) remained almost constant, (3) the intensity value (I) increased, and (4) the saturation value (S) decreased.

That is to say, as the scratch force (s) increased along the scratch path, whitening occurred due to the increased light scattering near the scratched groove caused by the surface damage.

The scratch-induced whitening of the material leads to change in the color coordinates. Specifically, the whitening results in change of the intensity (I) and saturation (S) values in the HSI color model, whereas the hue (H) values remains constant without regard thereto.

To see the intensity (I) and saturation (S) profile along the scratch path in detail in FIG. 14, their slopes keep changing as the degree of the scratch-induced surface damage increases.

For example, the intensity (I) value remains constant in the scratch-uninduced region (no damage zone in FIG. 14). However, it increases in the scratch-induced region (mar zone) after passing through the first color transition point. Then, after remaining even, it increases again after passing through the second color transition point. This pattern is shown repeatedly.

The saturation (S) value remains constant initially. However, it decreases in the scratch-induced region (mar zone) after passing through the first color transition point. Then, after remaining even, it decreases again after passing through the second color transition point. This pattern is shown repeatedly.

This indicates that the changing slope of intensity (I) value and saturation (S) value may be an indicator of change in the color coordinates, especially change in the degree of surface damage.

The visibility of the scratch formed on the material surface is related to intensity (I), saturation (S) and scratch resistance (8), and the scratch visibility index may be calculated from a combination thereof.

Observation was made using an optical microscope in order to correlate the color transition points of FIG. 14 with the shape of the surface damage.

Figure 15:
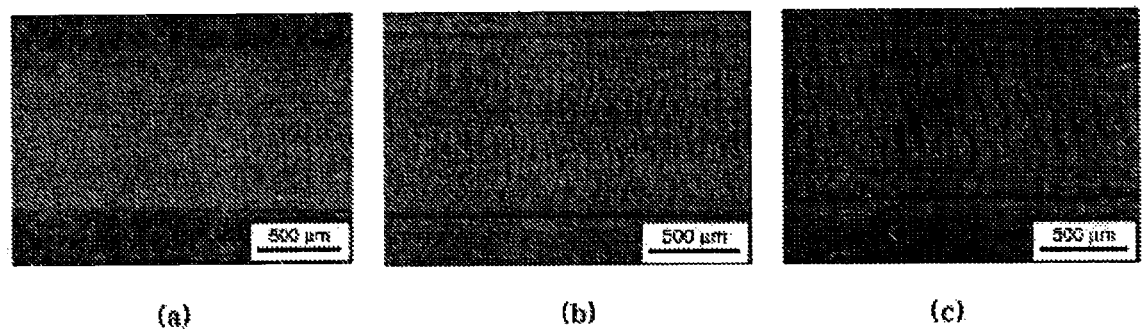
FIG. 15 shows optical micrographs of the regions I, II and III in FIG. 13, which show surface damages around the first color transition point (a), the second color transition point (b), and the third color transition point (c).

FIG. 15 shows optical micrographs of the regions I, II and III in FIG. 13, which respectively show surface damages around the first color transition point (a), the second color transition point (b), and the third color transition point (c).

As shown in FIG. 15, the region I shows a mar, which is a relatively light surface damage, and the region II shows a ripple pattern of overlapped surface damages. It is also observed with naked eyes as whitening. In this example, the more distinctly discernible, second color transition point was determined as "the onset of scratch visibility".

And, the "scratch visibility index" is determined as a combination [$I_c$, $S_c$, $\vec{R}_c$] of the intensity ($I_c$), saturation ($S_c$) and scratch resistance ($\vec{R}_c$) at the onset of scratch visibility.

The test result is given in Table 4 as the scratch visibility index (SVI).

TABLE 4

| Test condition | Scratch visibility index (SVI) [$I_c$, $S_c$, $\vec{R}_C$] |
|---|---|
| 1 to 30N | [51.3, 50.4, 16.2] |

The region III, which is near the third color transition point, shows a wider ripple pattern as the scratch damage increased.

Therefore, it can be seen that the present invention allows quantitative evaluation of the visibility of the mar- and scratch-induced surface damage formed on polymeric and coating materials as a quantitated scratch visibility index.

Further, as demonstrated in Example 2, the quantitated value representing the visibility of the surface damage is free from errors resulting from the operator or the evaluation environment.

The quantitative evaluation method according to the present invention is widely applicable without regard to the color or surface pattern of the material surface. And, the operator may randomly select the color model for analysis of the surface damage without limitation.

While the present invention has been described with respect to the specific embodiments, it will be apparent to those skilled in the art that various changes and modifications may be made without departing from the spirit and scope of the invention as defined in the following claims.

What is claimed is:

1. A method for quantitative evaluation of scratch-induced damage formed on the surface of polymeric and coating materials, comprising:
   preparing a test specimen of polymeric and coating materials;
   inducing a scratch damage on the surface of the test specimen;
   representing the scratch damage formed on the test specimen as corresponding color coordinates; and calculating a quantitated scratch damage index from a combination of a load applied to the surface of the test specimen and the color coordinates corresponding to the scratch damage.

2. The method for quantitative evaluation of scratch-induced damage on polymeric and coating materials according to claim 1, wherein said inducing the scratch damage comprises forming the scratch damage on the surface of the test specimen using a scratch tip capable of area-contact or line-contact.

3. The method for quantitative evaluation of scratch-induced damage on polymeric and coating materials according to claim 1, wherein said inducing the scratch damage comprises forming the scratch damage by applying a constant load to the surface of the test specimen.

4. The method for quantitative evaluation of scratch-induced damage on polymeric and coating materials according to claim 1, wherein said representing the scratch damage as corresponding color coordinates comprises steps of: obtaining an image by scanning the scratch damage formed on the surface of the test specimen; and representing color values of the obtained image as color coordinates of a 2-dimensional or 3-dimensional color model using a color analysis software.

5. The method for quantitative evaluation of scratch-induced damage on polymeric and coating materials according to claim 1, wherein said representing the scratch damage as corresponding color coordinates is conducted by using a color analysis profiler.

6. The method for quantitative evaluation of scratch-induced damage on polymeric and coating materials according to claim 1, wherein a color analysis technique using a 2-dimensional or 3-dimensional color model is used to analyze the scratch damage formed on the surface of the test specimen.

7. The method for quantitative evaluation of scratch-induced damage on polymeric and coating materials according to claim 1, wherein the scratch damage is in a form of simple damage, in which scratches are formed along one direction, or in a form of complex damage, in which further scratches having another direction with the simple damage is added to the simple damaged test specimen.

8. The method for quantitative evaluation of scratch-induced damage on polymeric and coating materials according to claim 4, wherein the color analysis software is one capable of performing color analysis as a whole or as a part of the surface damage area of the test specimen.

9. The method for quantitative evaluation of scratch-induced damage on polymeric and coating materials according to claim 4, wherein the color analysis software is capable of performing continuous measurement on the width and length of the whole scratch formed on the surface of the test specimen.

10. The method for quantitative evaluation of scratch-induced damage on polymeric and coating materials according to claim 4, wherein, when a scratch tip is in line-contact with the surface of the test specimen, the color analysis software represents the color coordinates of each row j of the image corresponding to the scratch direction as an average value of all the color coordinate values of the row j.

11. The method for quantitative evaluation of scratch-induced damage on polymeric and coating materials according to claim 1, wherein the scratch damage index is calculated on the basis of degree of scratch damage ($\Delta D$) and scratch strength ($\vec{S}_s$) in case of area-contact between the scratch tip and the surface of the test specimen, and is calculated on the basis of degree of scratch damage ($\Delta D$) and scratch resistance ($\vec{R}_s$) in case of line-contact between the scratch tip and the surface of the test specimen.

12. A method for quantitative evaluation of visibility of scratch-induced damage formed on the surface of polymeric and coating materials, comprising:
preparing a test specimen of polymeric and coating materials;
inducing a scratch damage on the surface of the test specimen;
scanning the scratch-induced surface damage to obtain an image;
performing color analysis on the image for each pixel and profiling the change in surface damage as color coordinates using a color analysis software; and
graphically representing the change in the color coordinates and a load applied to the surface of the test specimen and calculating a scratch visibility index (SVI) from a determination and a combination of the components relating only to scratch visibility.

13. The method for quantitative evaluation of visibility of scratch-induced damage on polymeric and coating materials according to claim 12, wherein said inducing the scratch damage comprises forming the scratch damage on the surface of the test specimen using a scratch tip capable of line-contact.

14. The method for quantitative evaluation of visibility of scratch-induced damage on polymeric and coating materials according to claim 12, wherein said inducing the scratch damage comprises forming the scratch damage by applying a linearly increasing load to the surface of the test specimen.

15. The method for quantitative evaluation of visibility of scratch-induced damage on polymeric and coating materials according to claim 12, wherein the surface damage area of the test specimen is analyzed using a color analysis technique using a 3-dimensional color model.

16. The method for quantitative evaluation of visibility of scratch-induced damage on polymeric and coating materials according to claim 12, wherein, in said profiling as color coordinates, the color analysis software is one capable of performing color analysis as a whole or as a part of the surface damage area of the test specimen.

17. The method for quantitative evaluation of visibility of scratch-induced damage on polymeric and coating materials according to claim 12 or 16, wherein the color analysis software represents the color coordinates of each row j of the image corresponding to the scratch direction as an average value of all the color coordinate values of the row j.

18. The method for quantitative evaluation of visibility of scratch-induced damage on polymeric and coating materials according to claim 12, wherein the color analysis software is capable of performing continuous measurement on the width and length of the whole scratch formed on the surface of the test specimen.

19. The method for quantitative evaluation of visibility of scratch-induced damage on polymeric and coating materials according to claim 12, wherein the scratch visibility index is represented as a combination $[I_c, S_c, \vec{R}_c]$ of intensity ($I_c$), saturation ($S_c$) and critical scratch resistance ($\vec{R}_c$) when the onset of the surface damage of the test specimen is perceived.

20. The method for quantitative evaluation of visibility of scratch-induced damage on polymeric and coating materials according to claim 13, wherein the scratch tip is contacted with the surface of the test specimen along a horizontal direction to induce the scratch damage with a constant distance and constant speed.

\* \* \* \* \*